United States Patent [19]
Grady

[11] Patent Number: 4,695,361
[45] Date of Patent: Sep. 22, 1987

[54] OXYGEN SENSOR

[75] Inventor: Mark P. Grady, Norristown, Pa.

[73] Assignee: Seatronics, Inc., Hatboro, Pa.

[21] Appl. No.: 864,492

[22] Filed: May 19, 1986

Related U.S. Application Data

[63] Continuation-in-part of Ser. No. 794,553, Nov. 4, 1985, abandoned.

[51] Int. Cl.[4] .......................................... G01N 27/46
[52] U.S. Cl. .................................................. 204/415
[58] Field of Search ................ 204/415, 1 P; 128/635

[56] References Cited

U.S. PATENT DOCUMENTS

| | | | |
|---|---|---|---|
| 2,805,191 | 9/1957 | Hersch | 204/1 T |
| 3,028,317 | 4/1962 | Wilson et al. | 204/1 T |
| 3,050,371 | 8/1962 | Dowson et al. | 436/138 |
| 3,227,643 | 1/1966 | Okun et al. | 204/1 T |
| 3,235,477 | 2/1966 | Keyser et al. | 204/415 |
| 3,239,444 | 3/1966 | Heldenbrand | 204/415 |
| 3,260,656 | 7/1966 | Ross | 204/1 T |
| 3,272,725 | 9/1966 | Garst | 204/1 T |
| 3,315,271 | 4/1967 | Hersch et al. | 204/409 |
| 3,322,662 | 5/1967 | Mackereth | 204/415 |
| 3,429,796 | 2/1969 | Lauer | 204/415 |
| 3,503,861 | 3/1970 | Volpe | 204/402 |
| 3,577,332 | 5/1971 | Porter et al. | 204/408 |
| 3,616,410 | 10/1971 | Shioffer et al. | 204/415 |
| 3,711,395 | 1/1973 | Plank et al. | 204/408 |
| 3,767,552 | 10/1973 | Lauer | 204/408 |
| 3,826,730 | 7/1974 | Watanabe et al. | 204/415 |
| 3,929,588 | 12/1975 | Parker et al. | 204/1 T |
| 4,017,373 | 4/1977 | Shaw et al. | 204/432 |
| 4,207,161 | 6/1980 | Pegnim | 204/408 |
| 4,277,322 | 7/1981 | Kane | 204/408 |
| 4,324,632 | 4/1982 | Tantram et al. | 204/415 |
| 4,367,133 | 1/1983 | Lauer | 204/408 |
| 4,406,770 | 9/1983 | Chan et al. | 204/406 |
| 4,435,268 | 3/1984 | Martin | 204/408 |

FOREIGN PATENT DOCUMENTS 3029153  3/1982  Fed. Rep. of Germany ...... 204/415

Primary Examiner—T. Tung
Attorney, Agent, or Firm—William H. Eilberg

[57] ABSTRACT

The present invention is an oxygen sensor, having the form of an electrochemical cell, of the galvanometric type. Oxygen from the outside environment enters the cell through a gas-permeable liquid-impermeable membrane, and supports an electrochemical reaction which generates an electric current. The amount of current produced is proportional to the amount of oxygen entering the cell. The cathode of the cell is a flat, perforated gold disk, and the connection between the cathode and an external terminal is made with a spring which is compressed between the terminal and the cathode. In order to seal the cell against leakage of liquid, the cathode is enclosed within an O-ring, and the membrane is placed directly over the cathode and O-ring combination. In an alternative embodiment, suitable for use in high-pressure environments, the cell is provided with an expansion diaphragm. In the latter embodiment, the sealing is accomplished by laying the membrane over the cathode, and placing a separate disk, surrounded by a gasket, over the membrane.

19 Claims, 5 Drawing Figures

OXYGEN SENSOR

CROSS-REFERENCE TO PRIOR APPLICATION

This is a Continuation-In-Part of U.S. patent application Ser. No. 794,553, filed Nov. 4, 1985, now abandoned.

BACKGROUND OF THE INVENTION

The present invention relates to the field of electrochemical oxygen sensors which provide a quantitative indication of the amount of oxygen in an environment.

Electrochemical oxygen sensors have been known in the art for a long time, and include the so-called galvanometric cells and the so-called polarographic cells. Galvanometric cells are, in effect, miniature fuel cells which generate an electric current when oxygen comes into contact with the electrodes. Polarographic cells require an external voltage source. The cell of the present invention is of the galvanometric type, but the structure disclosed herein could also be applied to cells of the polarographic type.

Examples of electrochemical cells used as oxygen sensors are shown in U.S. Pat. Nos. 3,429,796 and 3,767,552. Both of these patents show electrochemical cells, of the galvanometric type, having a cathode and anode, disposed within a housing, an electrolyte contacting the cathode and anode, and a gas-permeable liquid-impermeable membrane which is spread over the cathode. Oxygen from outside the cell can enter the cell through the membrane, but the liquid electrolyte cannot pass through the membrane in the other direction.

The cathodes in the cells described in the above-mentioned patents provide a site for reduction of oxygen into hydroxyl ions. The hydroxyl ions react with the anode to form an oxide of the anode, while also releasing electrons. These oxidation and reduction reactions together produce an electric current when a load is connected across the electrodes.

While the operation of an oxygen sensor cell is, in theory, quite simple, many practical problems arise in the design of such cells. For example, it is necessary that the cell be completely sealed from the outside environment. If the electrolyte leaks out, the effectiveness of the cell will be gradually reduced, and the overall life of the cell will be shortened. It is also important that leakage not occur from the outside into the cell.

Electrochemical oxygen sensors should also show linearity, i.e. the current produced should in fact be proportional to the amount of oxygen in the outside environment. Moreover, the cell must be capable of generating a current as soon as even a small amount of oxygen enters the cell.

Another problem encountered with electrochemical oxygen sensors is breakage of the components during assembly, shipment, or use. In the sensors of the prior art, it has been customary to connect the electrodes to their terminals by spot welding a wire to the electrodes and the terminals. This type of connection sometimes breaks during handling, or when the components of the cell are being assembled.

The present invention comprises an improvement in an electrochemical cell structure, wherein the cell is well-protected against leakage to and from the outside, and the gas diffusion membrane is protected from damage caused by sharp objects. The cell is easy to assemble, and the connection between the cathode and its terminal is such as to minimize the likelihood of breakage. Embodiments of the invention are described for use in both normal and hyperbaric environments.

SUMMARY OF THE INVENTION

The oxygen sensor of the present invention comprises a cathode and an anode disposed within a liquid electrolyte bath, the electrodes and electrolyte being contained within an insulating housing. The connection between the cathode and the outside terminal is made by a spring which rests, under compression, on the cathode.

The cathode of the oxygen sensor is surrounded by an O-ring seal. A gas-permeable liquid-impermeable membrane, made of a hydrophobic material such as Teflon, is laid over the cathode. The diameter of the membrane is at least as great as that of the O-ring, and is therefore greater than that of the cathode. Laid against the Teflon membrane is a sintered disk, which tends to distribute incoming gas more uniformly to the cathode, and protects the gas diffusion membrane from damage by sharp objects. Both the membrane and the sintered disk are held against the cathode by a perforated metal disk and a retaining means. The diameter of the cathode is therefore less than the diameter of all the components which are laid over it. Specifically, the O-ring seal contacts the adjacent hydrophobic membrane; the cathode itself does not extend beyond the O-ring. The structure described provides a reliable, water-tight seal, which prevents migration of liquid in either direction through the seal.

In another embodiment, suitable for use in a high-pressure environment, the cell has an expansion diaphragm at the end of the cell opposite the cathode. Laid over the cathode is a hydrophobic gas diffusion membrane, similar to that described above. Centrally located on the membrane are a sintered disk, a perforated metallic disk, and a perforated plastic disk. The membrane has substantially the same diameter as that of the cathode. The entire assembly is sealed by an O-ring seal which is disposed around the perforated plastic disk and compressed against the gas diffusion membrane onto the cathode. The connection of the cathode to its terminal is also by means of a spring, held under compression against the cathode.

It is therefore an object of the present invention to provide an oxygen sensor comprising an electrochemical cell which is well-protected against leakage of fluid into or out of the cell.

It is another object of the invention to provide a sensor as described above, wherein the diffusion membrane is protected from physical harm.

It is another object to provide an oxygen sensor as described above, wherein the sensor is suitable for operation in high-pressure environments.

It is another object to provide an oxygen sensor wherein the connection between the cathode terminal and the cathode is not prone to breakage, and wherein the connection provides for reliable operation.

It is another object of the invention to provide an oxygen sensor which reacts speedily, and linearly, to the presence of oxygen in the outside environment, to produce an electric current giving an accurate indication of the amount of oxygen present.

It is another object of the invention to prolong the life of electrochemical oxygen sensors.

It is another object of the invention to provide an oxygen sensor which can be easily assembled, with minimal risk of breakage of its components during assembly.

Other objects and advantages of the invention will be apparent to those skilled in the art, from a reading of the following brief description of the drawings, the detailed description of the invention, and the appended claims.

DETAILED DESCRIPTION OF THE INVENTION

The oxygen sensor of the present invention is an electrochemical cell, of the galvanometric type, in which the current generated by the cell is proportional to the number of molecules of oxygen entering the cell. In the preferred embodiment, the cell has a gold cathode, a lead anode, a suitable electrolyte, such as potassium hydroxide, and a gas-permeable liquid-impermeable diffusion membrane laid over the cathode.

The gold of the cathode is not consumed in the chemical reactions in the cell, but instead serves as a reaction site for the reduction of oxygen molecules into hydroxyl ions. The reaction at the cathode is:

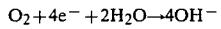

$$O_2 + 4e^- + 2H_2O \rightarrow 4OH^-$$

The reaction at the anode is:

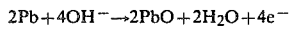

$$2Pb + 4OH^- \rightarrow 2PbO + 2H_2O + 4e^-$$

In other words, the lead anode is oxidized to lead oxide, giving up electrons, which, when an external load is connected to the electrodes, travel through the circuit to reduce more oxygen at the cathode.

Figure 3:
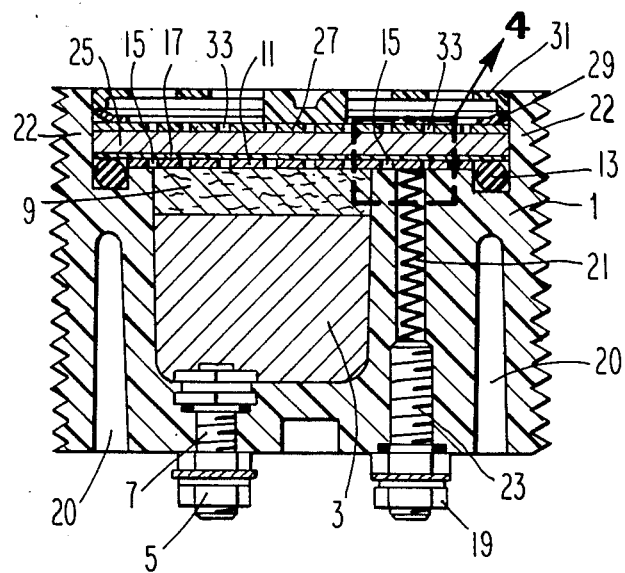
FIG. 3 is a cross-sectional view of the oxygen sensor of the present invention, taken along the line 3—3 of FIG. 1.

The overall structure of the cell according to the present invention is illustrated in FIG. 3, which is a cross-sectional view of the cell. The cell is disposed in a housing 1, which should be made of an insulating material. In the preferred embodiment, housing 1 is made of molded plastic. The housing defines a cavity for lead anode 3, which is connected to anode terminal 5 by screw 7. It is understood that various forms of anode construction can be used.

A flexible separator 9 is disposed between anode 3 and cathode 11. The separator keeps the cathode and the anode apart, preventing a short circuit between the electrodes. The separator can therefore be made of any suitable insulating material. The thickness of the separator is shown to be approximately 4-5 times that of the cathode, but this ratio can be varied. The cathode, in this embodiment, can be a perforated gold-plated stainless steel disk. The perforations 15 are distributed around the disk in a generally uniform arrangement. Cathode 11 is mounted within a gasket, or O-ring seal, designated by reference numeral 13, the diameter of the cathode being less than that of the gasket. In one embodiment, the disk comprising the cathode may be about 0.008 inches thick, but this dimension is only given by way of example, and does not limit the scope of the invention.

The cathode 11 is electrically connected to cathode terminal 19 through spring 21, which is in compression and rests on the surface of the cathode. The other end of spring 21 rests on the end of screw 23. The spring is free, i.e. it is not welded or soldered to the cathode or to the screw. Good electrical contact is insured by compression of the spring within its cavity.

Figure 4:
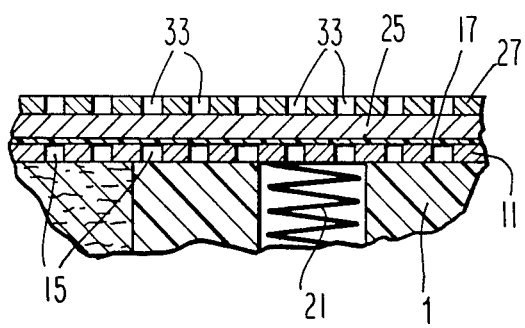
FIG. 4 is a detailed drawing of the region in FIG. 3 indicated by the dotted line 4.

The cell of the present invention comprises a unique arrangement of the disks and the membrane. The specifics of this structure are visible both in FIG. 3, and in FIG. 4, which is an expanded view of the area within dotted line 4 in FIG. 3. A gas-permeable liquidimpermeable membrane 17 is laid over the cathode. In the preferred embodiment, membrane 17 is constructed from Teflon (Teflon is a trademark of the DuPont Company). The membrane 17 is quite thin compared to the cathode. The diameter of membrane 17 is substantially equal to the outside diameter of gasket 13.

Disk 25 is laid over membrane 17. Disk 25 is relatively thick in comparison to the cathode. Disk 25 is preferably constructed of sintered material which presents a substantial amount of open area to the gas entering the cell. This disk, which allows gas, but not liquid, to flow through it, diffuses the gas entering the cell before it reaches the cathode, and protects the gas diffusion membrane from damage. The diameter of disk 25 is substantially equal to that of membrane 17.

The sintered disk 25 diffuses and distributes the oxygen entering the cell, after the oxygen has passed through the relatively large holes in the perforated disk. The sintered disk thus helps to insure that the complete surface of the membrane 17 will be utilized. Virtually any sinterable material may be used to construct the sintered disk, and a very wide range of thicknesses and porosities may be used. For example, satisfactory cells have been made using sintered metals, such as sintered stainless steel or bronze and also using sintered plastics, such as Teflon, polyethylene, and polyvinylidene fluor. The thicknesses of the sintered disks used have ranged from 0.1 to 0.01 inches, and the mean pore sizes of these disks have ranged from 20 to 100 microns. These ranges, however, are not to be construed as limiting; sintered disks having thicknesses and/or pore sizes outside these ranges can also be used successfully.

In most applications, no particular type of sintered material is preferable for use as a sintered disk. However, if the sensor is to be used in an environment in which water droplets may impinge on the face of the sensor, it is helpful to use a hydrophobic material for the sintered disk. For example, one could make the sintered disk of polyethylene or polytetrafluoroethylene (PTFE), also known as "Teflon". But if the sensor is being used in a dry environment, there is no reason to use a hydrophobic material, and, in fact, it may be preferable to use another type of material, such as a metal, which is hydrophilic, in order to obtain other advantages, such as structural strength.

The membrane 17 and disk 25 are covered by perforated disk 27. In the preferred embodiment, disk 27 is almost identical to the cathode, except for its diameter, and except for the fact that disk 27 is not gold-plated.

Thus, disk 27 can be constructed of stainless steel, and, having a thickness substantially equal to that of the cathode, and having a plurality of generally uniformly distributed perforations 33. The diameter of disk 27 is substantially equal to the diameters of membrane 17 and disk 25, and is therefore greater than the diameter of the cathode. Disk 27, in conjunction with perforated disk 25, protects the membrane 17 from damage.

Figure 1:
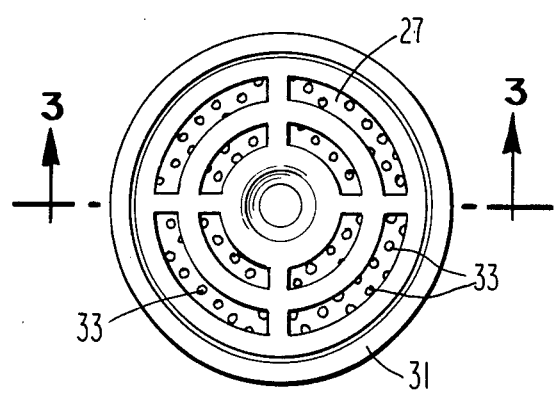
FIG. 1 is a top view of the oxygen sensor of the present invention, showing the side of the sensor where the oxygen enters.

The entire assembly of the cathode, membrane, and disks is held within a recess defined by the top portion 22 of housing 1. The components are clamped together by retaining ring 29 and protective plastic cap 31. This cap is more clearly illustrated in the top view of FIG. 1, in which the perforations 33 of disk 27 are visible.

Figure 2:
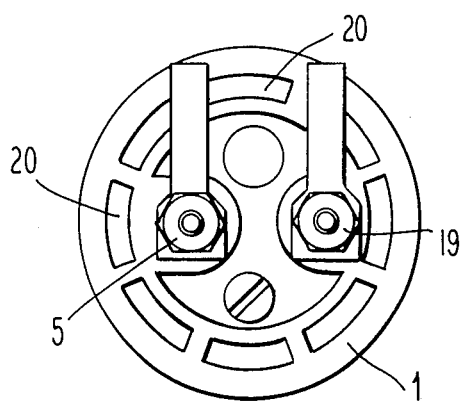
FIG. 2 is a bottom view of the oxygen sensor of the invention, showing the terminals for connection to an external electrical circuit.

The structure of the bottom of the cell is illustrated in FIG. 2. This view shows anode terminal 5 and cathode terminal 19, disposed on housing 1. The figure also shows recesses 20, which facilitate the molding of the housing from hot plastic material. Two of these recesses are also seen in FIG. 3.

Figure 5:
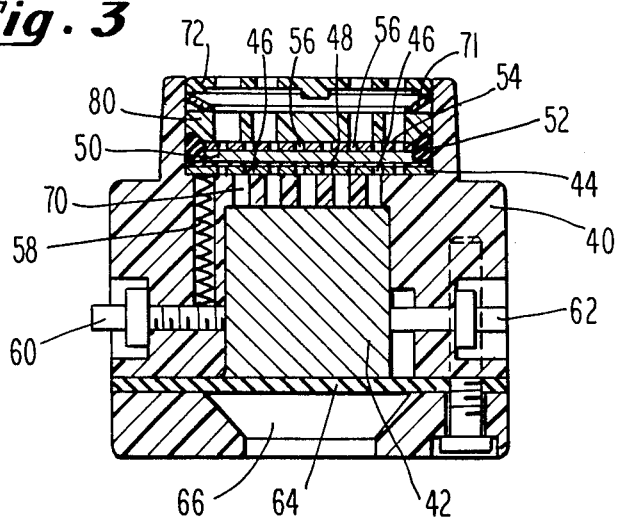
FIG. 5 is a cross-sectional view, similar to that of FIG. 3, showing an alternative embodiment of the oxygen sensor, this embodiment being suitable for use in high-pressure environments.

The spring 21 provides a simple and reliable means of connecting the cathode terminal to the cathode. In the prior art, it has been common to weld a wire to the cathode, and to the cathode terminal. When this means of attachment is employed, the wire sometimes breaks off from the cathode and/or the terminal during assembly of the cell. In the present invention, spring 21 essentially prevents such breakage during assembly. It is quite easy to attach the cathode to the cathode terminal in the the present invention: the spring is simply inserted into its cavity, so that it rests upon the cathode, and then screw 23 is threaded into place so as to compress the spring. In the cell of FIG. 5, to be discussed below, the spring is inserted into its cavity before the cathode and its associated parts are assembled, and the cathode, the membrane, the disks, and the cap are then placed into position. The spring will then be automatically compressed.

The sealing structure disclosed herein provides a substantially leak-proof cell. Due to the hydrophilic nature of metals, such as the gold of the cathode, the hydroxyl ions tend to migrate to all parts of the cathode. If the sealing means of the cell were between the gasket 13 and the cathode, some leakage would be likely. In the present invention, a seal is formed between the gasket 13 and the hydrophobic membrane 17. The diameter of cathode 13 is intentionally chosen to be less than that of the gasket, and less than the diameters of the other components, to enhance the quality of the seal. Moreover, because of the compression transmitted from retaining ring 29, the layers of disks and membranes are forced tightly against each other, leaving virtually no path even for a tiny flow of liquid in or out of the cell.

FIG. 5 shows a cross-sectional view, similar to that of FIG. 3, of an alternative embodiment of the invention. This embodiment has an expansion diaphragm which makes the sensor suitable for use in high-pressure environments. The sensor is formed of housing 40, anode 42, and cathode 44. As in the first embodiment, cathode 44 is perforated, and holes 46 in the cathode are visible in FIG. 5. Membrane 48, preferably made of Teflon material, as was used for membrane 17 of the first embodiment, is laid over cathode 44, and a disk 50, preferably made of the same sintered material of the first embodiment, is laid over membrane 48. Metal disk 54 and gasket 52 are laid over disk 50. Disk 54, as in the first embodiment, is perforated, and holes 56 are visible in disk 52, in FIG. 5.

A plastic sealing disk 80 is placed over gasket 52 and metal disk 54. The bottom side of the disk 80 is beveled to accommodate the gasket, as shown. The plastic disk 80 is pressed against the afore-mentioned parts by retaining ring 71, thereby holding the components in place. The sensor may be covered by protective cap 72.

The sensor in FIG. 5 also has a spring 58 which electrically connects the cathode 44 to cathode terminal 60. Anode terminal 62 is provided on the other side of the housing. Diaphragm 64, preferably made of rubber or other similar material, is disposed at the end of the cell opposite the cathode, and defines an expansion chamber 66.

Housing 40 also has a plurality of holes 70. The material between these holes comprises a separator for the cathode and the anode, and also supports the cathode. The holes permit the passage of electrolyte and gas. This structure takes the place of the separator 9 of FIG. 3.

The sealing structure of the embodiment of FIG. 5 thus differs somewhat from that of the first embodiment. In FIG. 5, the cathode and the Teflon membrane both have substantially the same diameter. The gasket, or O-ring, also has substantially the same diameter as the cathode, but the sintered disk and the perforated metal disk 54 have a smaller diameter. The gold-plated cathode does not touch the gasket at all, the gasket being located above the hydrophobic membrane. Thus, FIG. 5 also provides an excellent means of sealing the cell against leakage of liquid.

It is understood that the present invention can be modified in many ways, within the spirit of the disclosure. As stated above, the dimensions and thicknesses suggested for the components are only given as examples, and are not intended to limit the invention to those dimensions. Even the ratios of the thicknesses of the layers can be changed somewhat. It is also understood that the invention is not limited to the particular types of materials mentioned above; other gas-permeable liquid-impermeable substances, whether or not currently known or available, could be substituted for the Teflon membranes, within the scope of the invention. The cathode, anode, and electrolyte can be made of other materials, which may enhance operation under particular conditions. The invention is not limited to galvanometric cells, but can also be used in polarographic cells.

It has also been found that the particular disk and membrane arrangement described with respect to the hyperbaric sensor can also be used in the ordinary sensor, and vice versa. That is, the "sandwich" structures, illustrated in FIGS. 3 and 5, are not restricted to use in hyperbaric or non-hyperbaric cells. FIG. 5 is suited to hyperbaric environments because of its expansion diaphragm, not due to the sandwich structure.

The specific embodiments described above are therefore only illustrative. It is understood that various modifications, such as those described above, and others, should be deemed within the spirit and scope of the following claims.

What is claimed is:

1. An oxygen sensor, comprising:
    (a) means defining a housing,
    (b) an anode disposed within the housing, the anode being connected to an anode terminal,
    (c) a cathode disposed within the housing, the cathode comprising a perforated metallic disk, the cathode being kept apart from the anode by an insulating separator, the cathode being disposed within a gasket in a recess in the housing, (d) an electrolyte disposed within the housing and contacting the cathode and anode, (e) a gas-permeable liquid-impermeable membrane having a diameter substantially equal to that of the gasket, the membrane being disposed adjacent the cathode, on the side of the cathode opposite the anode, (f) a sintered disk, having a diameter substantially equal to that of the membrane, the sintered disk being disposed adjacent the membrane, (g) means for holding the membrane and the sintered disk against each other and against the cathode, and (h) spring means, disposed within a cavity in the housing, the spring means being held in compression between the cathode and a cathode terminal, wherein the electrical connection between the cathode and the cathode terminal is completed by the spring means.

2. The sensor of claim 1, wherein the holding means comprises a second perforated metallic disk, disposed against the membrane and the sintered disk, within the recess in the housing.

3. The sensor of claim 2, wherein the thickness of the sintered disk is at least five times that of the membrane.

4. The sensor of claim 3, wherein the membrane is constructed of polytetrafluoroethylene.

5. The sensor of claim 4, wherein the sintered disk is constructed of a material having a mean pore size in the range of about 20 to about 100 microns.

6. The sensor of claim 2, wherein the cathode comprises a gold-plated stainless steel disk.

7. An oxygen sensor, comprising:
(a) means defining a housing, the housing being constructed of an insulating material,
(b) an anode disposed within the housing, the anode being connected to an anode terminal,
(c) a cathode disposed within the housing, the cathode comprising a perforated metallic disk, the cathode being held apart from the anode by a perforated separator, the cathode being disposed within a recess in the housing,
(d) an electrolyte disposed within the housing and contacting the cathode and anode,
(e) a gas-permeable liquid-impermeable membrane having a diameter substantially equal to that of the cathode, the membrane being disposed adjacent the cathode, on the side of the cathode opposite the anode,
(f) a sintered disk, the sintered disk being disposed adjacent the first membrane,
(g) a second perforated metallic disk, disposed within a gasket means, for holding the membrane and the sintered disk against each other and against the cathode, the diameters of the second perforated disk and of the sintered disk being substantially equal and being less than that of the membrane and the cathode, the second perforated disk and gasket means disposed within a recess in the housing, and
(h) spring means, disposed within a cavity in the housing, the spring means being held in compression between the cathode and a cathode terminal, wherein the electrical connection between the cathode and the cathode terminal is completed by the spring means.

8. The sensor of claim 7, wherein the thickness of the sintered disk is at least five times that of the first membrane.

9. The sensor of claim 8, wherein the membrane is constructed of polytetrafluoroethylene, and wherein the sintered disk is constructed of a material having a mean pore size in the range of about 20 to about 100 microns.

10. The sensor of claim 9, wherein the cathode comprises a goldplated stainless steel disk.

11. In an oxygen sensor comprising an electrochemical cell having a housing, a cathode, an anode, and an electrolyte disposed to contact the cathode and the anode, and a gas-permeable liquid-impermeable membrane disposed to allow gas from outside the cell to enter the cell, the sensor having a cathode terminal and an anode terminal for connecting an external load to the cathode and the anode, the cathode comprising a flat metal member, the improvement wherein the cathode comprises a perforated disk, the disk being disposed within a gasket, the gasket having a diameter larger than that of the disk, the cathode and gasket being disposed adjacent the gas-permeable liquid impermeable membrane, wherein the membrane has a diameter at least as large as that of the gasket, wherein the membrane and the gasket together seal the cell against leakage to the outside.

12. The improvement of claim 11, further comprising a spring means, disposed within a cavity within the cell, the cavity communicating with the cathode terminal and the cathode, wherein the spring means is held in compression within the cavity, and wherein the electrical connection between the cathode and the cathode terminal is completed by the spring means.

13. The improvement of claim 12, further comprising a sintered disk, disposed adjacent the membrane such that the membrane is located between the cathode and the sintered disk, the sintered disk having a diameter substantially equal to that of the membrane, and having a thickness at least five times that of the membrane, and wherein the cathode, membrane, and sintered disk are disposed within a recess defined by the housing.

14. In an oxygen sensor comprising an electrochemical cell having a cathode, an anode, and an electrolyte disposed to contact the cathode and the anode, a gas-permeable liquid-impermeable membrane disposed to allow gas from outside the cell to enter the cell, the sensor having a cathode terminal and an anode terminal for connecting an external load to the cathode and the anode, the cathode comprising a flat metal member, the improvement wherein the cathode comprises a perforated disk, the disk being disposed adjacent the gas-permeable liquid-impermeable membrane, the membrane having a diameter substantially equal to that of the cathode, the cell having a metallic perforated disk disposed within a gasket, the gasket having an outside diameter larger than that of the metallic disk and substantially equal to that of the cathode.

15. The improvement of claim 14, further comprising a spring means, disposed in a cavity within the cell, the cavity communicating with the cathode terminal and the cathode, wherein the spring means is held in compression within the cavity, and wherein the electrical connection between the cathode and the cathode terminal is completed by the spring means.

16. The improvement of claim 15, further comprising a sintered disk, disposed between the membrane and the metallic disk, the sintered disk having a diameter substantially equal to that of the metallic disk, the sintered disk having a thickness at least five times that of the membrane, and wherein the cathode, membrane, and sintered disk are disposed within a recess defined by the housing.

17. The improvement of claim 16, wherein the sintered disk and the metallic disk are located within the gasket.

18. The improvement of claim 17, further comprising a perforated plastic disk, disposed to be pressed upon the metallic disk and the gasket.

19. The improvement of claim 16, wherein the cathode and anode are held apart by a perforated separator, the separator being positioned to hold the cathode and the membrane in contact at substantially every point along their surfaces.

* * * * *